United States Patent [19]

Michel et al.

[11] Patent Number: 4,492,650

[45] Date of Patent: Jan. 8, 1985

[54] A54556 ANTIBIOTICS AND PROCESS FOR PRODUCTION THEREOF

[75] Inventors: Karl H. Michel; Ralph E. Kastner, both of Indianapolis, Ind.

[73] Assignee: Eli Lilly and Company, Indianapolis, Ind.

[21] Appl. No.: 423,948

[22] Filed: Sep. 27, 1982

[51] Int. Cl.³ .......................................... C07C 103/52
[52] U.S. Cl. ............................................. 260/112.5 R
[58] Field of Search ................................. 260/112.5 R Primary Examiner—Delbert R. Phillips
Attorney, Agent, or Firm—Charles W. Ashbrook; Arthur R. Whale

[57] ABSTRACT

Antibiotic A54556, a complex of 8 individual factors, produced by submerged, aerobic fermentation of new Streptomyces hawaiiensis NRRL 15010. The complex and the individual, separated factors are active against Staphylococcus and Streptococcus which are penicillin resistant.

6 Claims, 6 Drawing Figures

A54556 ANTIBIOTICS AND PROCESS FOR PRODUCTION THEREOF

SUMMARY OF THE INVENTION

This invention relates to antibiotic A54556 complex comprising several factors, including individual factors A, B, C, D, E, F, G, and H, and to the processes for producing the complex and separating the factors. Further, this invention relates to a biologically pure culture of the previously undescribed microorganism *Streptomyces hawaiiensis* NRRL 15010. The A54556 complex is produced by culturing the hitherto undescribed microorganism, *Streptomyces hawaiiensis* NRRL 15010, or an A54556-producing mutant or variant thereof, under submerged aerobic fermentation conditions.

These A54556 antibiotics are active as gram-positive antibacterials.

DESCRIPTION OF THE DRAWINGS

Infrared absorption spectra of A54556 factors A, B, C, D, E, and H, all in KBr pellet, are presented in the drawings as follows.

DETAILED DESCRIPTION OF THE INVENTION

Figure 1:
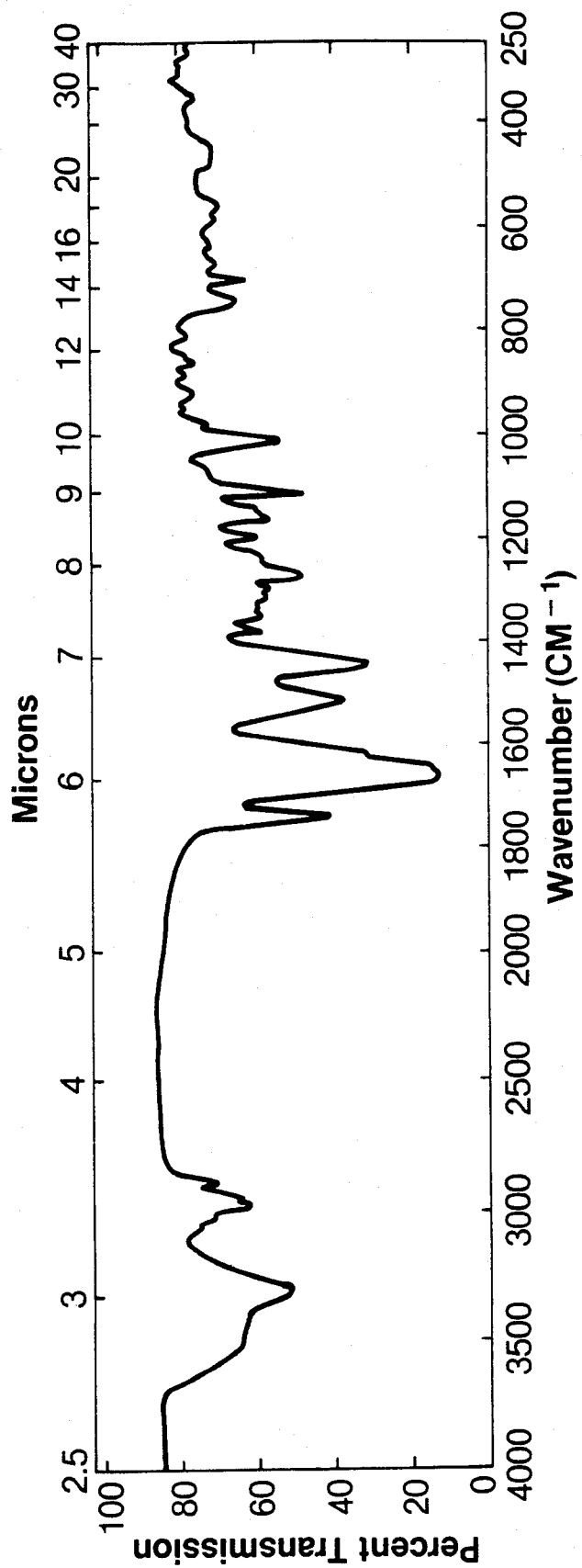
FIG. 1—A54556 factor A
FIG. 2—A54556 factor B
FIG. 3—A54556 factor C
FIG. 4—A54556 factor D
FIG. 5—A54556 factor E
FIG. 6—A54556 factor H

This invention relates to antibiotic substances. In particular, it relates to an antibiotic complex comprising several factors, including individual factors A, B, C, D, E, F, G, and H. This complex is produced by culturing a hitherto undescribed microorganism, *Streptomyces hawaiiensis*, NRRL 15010.

This invention further relates to a biologically pure culture of the hitherto undescribed organism *Streptomyces hawaiiensis* NRRL 15010. This organism was grown from a soil sample collected from a canyon in Arizona. For convenience, this culture has been designated in our laboratory as culture A54556.

The term "complex", as used in the fermentation art, and in this specification, refers to a mixture of co-produced individual factors. As will be recognized by those familar with antibiotic production by fermentation, the number and ratio of the individual factors produced in an antibiotic complex will vary, depending upon the fermentation conditions and the strain used.

Culture A54556 is classified as a strain of *Streptomyces hawaiiensis*, based upon a simultaneous culturing of *Streptomyces hawaiiensis* Cron, Whitehead, Hooper, Heinemann and Lein 1956, ATCC 12236; *Streptomyces janthinus*, ATCC 23925; *Streptomyces longisporus*, ATCC 23931; and *Streptomyces yokosukanensis*, ATCC 25520, using the methods recommended by the International Streptomyces Project (ISP) for the characterization of Streptomyces species [Nonomura, "Key for Classification and Identification of 458 Species of the Streptomycetes in ISP", *J. Ferment. Technol.* 52(2), 78-92(1974)], along with certain supplementary tests.

Culture A54556 is significantly different from *Streptomyces janthinus*, ATCC 23925, as the latter microorganism shows less growth in broth and on agar media. *S. janthinus* has a spore mass color in the white color series, and a reverse color that is yellowish gray. On Czapek's solution agar, *S. janthinus* has a distinctive violet pigment, and produces no melanoid pigment on tyrosine agar (ISP medium No. 7). The spore surface ornamentation of *S. janthinus* is predominantly warty, with some spines and also some smooth spore surfaces present.

Culture A54556 is also significantly different from *Streptomyces longisporus*, ATCC 23931. The morphology of *S. longisporus* appears different in that there are fewer spirals than Culture A54556, and on some media, no spirals are detected. The aerial spore mass color of *S. longisporus* is in the white color series predominantly, while the reverse color is more yellow than that of Culture A54556. Further, the spore surface ornamentation of *S. longisporus*, although spiny, differs in spine length and density from that of Culture A54556.

Culture A54556 is also different from *Streptomyces yokosukanensis*, ATCC 25520, but the differences are less than those with *S. janthinus* and *S. longisporus*. Thus, the morphology on ISP No. 2 and ISP No. 7 media appeared different, as *S. yokosukanensis* developed no spirals on either medium. Furthermore, the spore size and shape of Culture A54556 are different from those reported by Nakamura, "Studies on Antibiotic *Actinomycetes*, III. On Streptomyces Producing 9-β-D-Ribofuranosylpurine", *J. Antibiot.* 14(2), 94-97(1961). In addition, some smooth spore surfaces are observed in SEM micrographs of the *S. yokosukanensis* culture. Unlike Culture A54556, the *S. yokosukanensis* culture is predominantly in the red color species, and hydrolyzes and peptonizes skim milk, as well as reducing nitrate.

Culture A54556 is similar to *Streptomyces hawaiiensis*, ATCC 12236, in morphology, culturally, and in physiological characteristics, and the differences between these two cultures are minor. *S. hawaiiensis* produces a different morphology on ISP No. 5 and on Czapek's agar media from that produced by Culture A54556. The spore mass and reverse color of *S. hawaiiensis* are different from Culture A54556 in some cases.

Thus, comparison of Culture A54556 with the above-named cultures shows significant differences and some similarities. Our culture is considered to be a strain of *Streptomyces hawaiiensis*, ATCC 12236.

CHARACTERIZATION OF THE A54556 MICROORGANISM

Morphology

Culture A54556 produces well-developed aerial mycelia and sporophores which are coiled. The sporophores are long, and terminate with fairly compact coils of 2-6 turns. The sporophores bear chains of spores from 10-50 in number. The spores are oblong and have spiny ornamentation on the surface. Spore size ranges from about 0.59 to about 0.70 $\mu$M. in width, and from about 0.65 to about 1.53 $\mu$M. in length, with the average size being about 0.64 × 1.08 $\mu$M. The vegative hyphae measures 0.42 $\mu$M. in diameter.

Cultural Characteristics

A comparison of the growth characteristics of Culture A54556 and of *Streptomyces hawaiiensis*, ATCC 12236, on various media are presented in the following Table 1.

Color assignments are from the Tresner and Backus system [H. D. Tresner and E. J. Backus, "System of Color Wheels for Streptomyces Taxonomy", *Appl. Mi-* crobiol. 11, 335-338 (1956)], and *Color Harmony Manual* (4th Edition, Color Standards Department, Container Corporation of America, Chicago, Ill., 1958). The predominant color is 92. yellowish white, according to the ISCC-NBS system ("ISCC-NBS Centroid Color Charts Standard Sample No. 2106, "U.S. Department of Commerce. National Bureau of Standards. 1958).

TABLE

Cultural Characteristics of Cultures A54556 and *S. hawaiiensis*, ATCC 12236

| Medium | A54556 | S. hawaiiensis, ATCC 12236 |
|---|---|---|
| Yeast extract-malt extract agar (ISP medium No. 2) | Good growth, reverse 56. deep Br; good aerial mycelia (R)5cb to (Y)2ba, and light brown soluble pigment. | Abundant growth, reverse 72.d.OY; abundant aerial mycelia (W)b, and very light brown soluble pigment. |
| Oatmeal agar (ISP medium No. 3) | Good growth, reverse 90.gy.Y; good aerial mycelia (W)b to (GY)d, and no soluble pigment. | Good growth, reverse 90.gy.Y; good aerial mycelia (GY)2dc to 3fe, and no soluble pigment. |
| Inorganic salts-starch agar (ISP medium No. 4) | Abundant growth, reverse 72.d.OY; abundant aerial mycelia (Y)2ba; and no soluble pigment. | Good growth, reverse 56. deep Br; abundant aerial mycelia (R)5cb to (Y)2ba, and light brown soluble pigment. |
| Glycerol-asparagine agar (ISP medium No. 5) | Abundant growth, reverse 58.m.Br; abundant aerial mycelia (Y)2ba, and light brown soluble pigment. | Abundant growth, reverse 59.d.Br; good aerial mycelia (W)b to (R)5dc (light), and light brown soluble pigment. |
| Tyrosine agar (ISP medium No. 7) | Abundant growth, reverse 75. deep yBr; abundant aerial mycelia (R)5cb to (Y)2ba, and light brown soluble pigment. | Good growth, reverse 78.d.yBr; good aerial mycelia (W)b, and light brown soluble pigment. |
| Czapek's solution agar | Abundant growth, reverse 44.d.rBr; abundant aerial mycelia (Y)2ba to (R)5cb, and dark reddish-brown soluble pigment. | Abundant growth, reverse 72.d.OY; poor aerial mycelia (Y)2ba, and light brown soluble pigment. |

Carbon utilization was determined using ISP No. 9 basal medium to which filter-sterilized carbon sources were added to equal a final concentration of 1.0%. Plates were read after fourteen days incubation at 30° C.

The results of the carbon utilization tests carried out with Cultures A54556 and *S. hawaiiensis*, ATCC 12236 are set forth in Table 2, which follows.

TABLE 2

CARBON UTILIZATION

| Substrate: Carbon Sources Added to ISP No. 9 Basal Medium | Reactions at 14 Days of | |
|---|---|---|
| | A54556 | ATCC 12236 |
| No carbon source | − | − |
| D-Glucose | + | + |
| L-Arabinose | + | + |
| Sucrose | + | + |
| D-Xylose | + | + |
| i-Inositol | + | + |
| D-Mannitol | + | + |
| D-Fructose | + | + |
| L-Rhamnose | + | ± |
| Raffinose | + | + |
| Salicin | − | + |
| D-Galactose | + | + |
| Cellobiose | + | + |
| D-Maltose | + | + |
| Glycerol | + | + |
| D-Arabinose | + | ND |
| Melibiose | + | ND |
| D-Ribose | + | ND |
| Tween 20 | ± | ND |
| Tween 40 | + | ND |
| Tween 60 | + | ND |
| Tween 80 | + | ND |

TABLE 2-continued

CARBON UTILIZATION

| Substrate: Carbon Sources Added to ISP No. 9 Basal Medium | Reactions at 14 Days of | |
|---|---|---|
| | A54556 | ATCC 12236 |
| Tween 85 | ± | ND |

Key:
ND = not done
+ = carbon utilized
− = carbon not utilized
± = partial utilization

Cell Wall Studies

Using hydrolyzed whole cells of the organism, the presence of certain diagnostic sugars were determined. Isolated cell walls were used to determine the isomers of diaminopimelic acid.

The cell-wall sugars were determined using a modification of the procedure of M. P. Lechavalier ["Chemical Methods as Criteria for the Separation of Actinomycetes Into Genera." These methods were developed at workshops sponsored by the Subcommittee on Actinomycetes of the American Society of Microbiology, (Dr. Thomas G. Pridham, Convenor), and held at the Institute of Microbology, Rutgers University, The State University of New Jersey, New Brunswick, N.J., (1971)]. The isomers of diaminopimelic acid were determined using the method of Becker et al., *Appl. Microbiol.* 11, 421-423 (1964). The results of these cell-wall studies are set forth below.

| Test | Result Observed |
|---|---|
| Diagnostic sugars detected | Glucose, Ribose |
| Isomers of 2,6-diaminopimelic acid | LL-isomer |

The sensitivity of Culture A54556 to several antibiotics at specific concentrations was determined with sensitivity discs padded onto the surface of plates containing ISP medium No. 2 agar seeded with 2% inoculum of Culture A54556. The results are shown in Table 3, which follows.

TABLE 3

| | Antibiotic Sensitivity of Culture A54556 | | |
|---|---|---|---|
| Conc. | Antibiotic | Type Compound | A54556 |
| 30 mcg. | Cephalothin | β-lactam | − |
| 30 mcg. | Chloromycetin (CAP) | | trace |
| 15 mcg. | Erythromycin | macrolide | − |
| 30 mcg. | Novobiocin | | + |
| 10 units | Penicillin G | β-lactam | − |
| 5 mcg. | Rifampin | ansamacrolide | + |
| 10 mcg. | Streptomycin | aminoglycoside | + |
| 30 mcg. | Tetracycline | tetracycline | + |
| 30 mcg. | Vancomycin | glycopeptide | + |

Key:
+ = sensitive, zones of inhibition
− = resistant, no zones of inhibition

Melanoid pigment production was determined with ISP medium No. 1 (tryptone-yeast extract broth), ISP medium No. 6 (peptone-yeast extract iron agar), ISP medium No. 7 (tyrosine agar), and modified ISP medium No. 7, which has the tyrosine removed.

Starch hydrolysis was determined by testing for the presence of starch with iodine on ISP medium No. 4 (inorganic salts-starch agar) plates, according to the procedure of D. J. Blazevic and G. M. Ederer ("Principles of Biochemical Tests in Diagnostic Microbiology", John Wiley and Sons, Inc. New York, 1975).

Casein, esculin, hypoxanthine, tyrosine, xanthine decomposition, and lysozyme resistance were all determined by procedures described by D. Berd ["Laboratory Identification of Clinically Important Aerobic Actinomycetes," *Appl. Microbiol.* 25, 665–681 (1973)].

Sodium chloride and sucrose tolerance were measured by adding each to ISP medium No. 2 agar to equal the concentrations desired.

The pH range for growth was measured using the following buffers at 0.05 M in yeast-malt extract agar plates (ISP No. 2): citric acid, pH 3, 4, 5; 2-[N-morpholino]ethanesulfonic acid (MES), pH 6, (Sigma Chemical Co.); 3-[N-morpholino]propanesulfonic acid (MOPS), pH 7, (Aldrich Chemical Co.); N-[tris-(hydroxymethyl)methyl]glycine (Tricine), pH 8, (CalBiochem); 2-(cyclohexylamino)ethanesulfonic acid (CHES), pH 8.5, 9.0, 9.5, (P-L Biochemicals, Inc.); 3-cyclohexylamino-1,1-propanesulfonic acid (CAPS), pH 10.0, 10.5. The pH values of the agar plates were measured with a flat surface electrode prior to inoculation.

The methods of Blazevic and Ederer, supra, were followed for the catalase, phosphatase, and urease assays.

Additional characteristics of Culture A54556, determined by the methods outlined above, are listed in Table 4, which follows.

TABLE 4

| Additional Characteristics | |
|---|---|
| | A54556 |
| Casein decomposition | + |
| Catalase | + |
| D'Nase production | + |
| Esculin decomposition | + |
| Gelatin liquefaction | + |
| Hypoxanthine decomposition | + |

TABLE 4-continued

| Additional Characteristics | |
|---|---|
| | A54556 |
| Lysozyme resistance | − |
| Melanoid pigments | + |
| Morphology | Spiral |
| NaCl tolerance, percent | 8 |
| Nitrate reduction | − |
| pH range | 6.1–9.2 |
| Phosphatase | + |
| Skim milk | − |
| Spore shape | oblong |
| Spore size | 0.64 × 1.08 μM |
| Spore surface | spiny |
| Starch hydrolysis | − |
| Streptomycin sensitivity | + |
| Sucrose tolerance, percent | 35 |
| Temperature range °C. | 10–40 |
| Tyrosine decomposition | + |
| Urease production | + |
| Xanthine decomposition | + |

In Table 5, which follows, there is set forth a comparison of the similarities and differences between Cultures A54556 and *S. hawaiiensis*, ATCC 12236.

TABLE 5

| Comparison of Culture A54556 to ATCC 12236 | |
|---|---|
| Similarities | Differences |
| carbon utilization | antibiotic production |
| gelatin liquefaction | reverse color on 3 media |
| growth on agar slants | spore mass color on 4 media |
| growth in broth media | sporophore morphology on 2 media |
| melanoid pigment | |
| skim milk reaction negative: | |
| (no hydrolysis) | |
| (no coagulation) | |
| soluble pigment production | |
| spore mass color on ISP No. 3, No. 4 | |
| spore shape and size | |
| spore surface ornamentation (spiny) | |
| sporophore morphology (S) spiral | |
| starch hydrolysis negative or slight | |

The antibiotic substances of this invention are arbitrarily designated herein as A54556 antibiotics. The A54556 complex contains several individual factors which are designated A54556 factors A, B, C, D, E, F, G, and H. In discussions of utility, the term "A54556 antibiotic" will be used, for the sake of brevity, to denote a member selected from the group consisting of A54556 complex, and A54556 factors A, B, C, D, E, F, G, and H.

As many as eight antibiotic factors are recovered from the fermentation and are obtained as a mixture, the A54556 complex. It will be recognized that the ratio of the factors in the A54556 complex will vary, depending on the fermentation conditions employed. The individual factors A, B, C, D, E, F, G, and H are separated and isolated as individual compounds, as hereinafter described. The A54556 complex is soluble in the lower alcohols, i.e., methyl alcohol, ethyl alcohol, isopropyl alcohol, n-propyl alcohol, n-butyl alcohol, and the like, acetone, ethyl acetate, tetrahydrofuran, pyridine, and dimethyl sulfoxide, but is insoluble in water.

The following paragraphs describe the physical and spectral properties of the A54556 factors which have thus far been characterized.

A54556 FACTOR A

Antibiotic A54556 factor A is a tan, amorphous solid. Elemental analysis of A54556 factor A indicates that it has the following approximate percentage composition: 63.78 percent carbon, 7.08 percent hydrogen, 11.89 percent nitrogen, and 18.09 percent oxygen. As determined by electron impact and field desorption mass spectrometry, A54556 factor A has a molecular weight of 718. Based on the elemental analysis and the molecular weight, an empirical formula of $C_{38}H_{50}N_6O_8$ is assigned to factor A. Electrometric titration of factor A in 66 percent dimethylformamide in water showed no titratable groups.

The infrared absorption spectrum of A54556 factor A in KBr pellet is shown in the accompanying drawings as FIG. 1. The following distinguishable absorption maxima are observed: 3310 (medium), 2988 (weak), 2942 (very weak), 2895 (very weak), 1748 (medium), 1668 (strong), 1649 (shoulder), 1640 (very weak), 1523 (medium), 1450 (medium), 1388 (weak), 1361 (weak), 1325 (very weak), 1309 (very weak), 1280 (weak), 1251 (very weak), 1209 (weak), 1173 (weak), 1150 (very weak), 1123 (weak), 1020 (weak), 986 (very weak), 960 (very weak), 930 (very weak), 896 (very weak), 818 (very weak), 750 (weak), and 715 (weak) cm$^{-1}$.

The ultraviolet absorption maximum of A54556 factor A in ethanol is recorded in Table 6, which follows.

TABLE 6

| UV Absorption Maxima of A54556 Factors | |
|---|---|
| Factor | Max nm (ε) |
| A | 298 (34,000) |
| B | 298 (46,000) |
| C | 260 (30,000) |
| D | 263 (22,000) |
| E | 261 (21,000) |
| H | 260 (27,000) |

Amino-acid analysis of the acid-hydrolyzed antibiotic A54556 factor A showed the amino-acid compositions to be as recorded in Table 7, which follows:

TABLE 7

| Amino acid | Factor | | | | | |
|---|---|---|---|---|---|---|
|  | A | B | C | D | E | H |
| Serine | 1 | 1 | 1 | 1 | 1 | 1 |
| N—Methylalanine | 1 | 1 | 1 | 1 | 1 | 1 |
| Alanine | 1 | 1 | 1 | 1 | 1 | 1 |
| Proline | 1 | 2 | 1 | 1 | 2 | 1 |
| Methylproline | 1 | — | 1 | 1 | — | 1 |
| Phenylalanine | 1 | 1 | 1 | 1 | 1 | 1 |

The amino acids account for all of the nitrogen atoms and part of the carbon atoms in the molecule of each antibiotic A54556 factor, and form a peptide nucleus. The remainder of the carbon atoms are in a single acyl moiety, as established by observation of intense acylium ions present in the electron impact mass spectrum of each factor, and confirmed by the proton nuclear magnetic resonance spectrum in the case of the factor A. The chemical shifts, as determined in CDCl$_3$, of the acyl moiety of factor A are as follows:

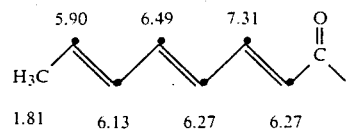

The chemical shifts of the amino acids of the peptide nucleus of factor A, appearing in the proton nmr of factor A, determined at 298° K. in CDCl$_3$, are set forth in Table 8, which follows:

TABLE 8

| Chemical Shifts of Amino Acids of Factors A, C, D, H | | | |
|---|---|---|---|
| Phenylalanine | | N—Methylalanine | |
| NH | 6.94 | N—CH$_3$ | 2.84 |
| α | 4.63 | α | 4.76 |
| β's | 2.98 | β | 1.51 |
| Ring o- | 7.16 | | |
| m- | 7.29 | | |
| p- | 7.20 | | |
| Serine | | Alanine | |
| NH | 6.53 | NH | 8.53 |
| α | 4.50 | α | 4.89 |
| β's | 4.85 | β | 1.38 |
|  | 3.54 | | |
| Methylproline | | Proline | |
| α | 4.45 | α | 5.28 |
| β's | 2.07 | β's | 2.37 |
|  | 1.80 | | 1.98 |
| γ | 2.37 | γ's | 2.17 |
| γ-CH$_3$ | 0.98 | | 1.98 |
| δ's | 3.48 | δ's | 3.75 |
|  | 3.09 | | 3.54 |

Antibiotic A54556 factor A is soluble in lower alcohols, i.e., methyl alcohol, ethyl alcohol, isopropyl alcohol, n-propyl alcohol and n-butyl alcohol, acetone, ethyl acetate, tetrahydrofuran, pyridine, and dimethyl sulfoxide, but is insoluble in water.

Based on the physical chemical properties described hereinbefore, the following structure is assigned to antibiotic A54556 factor A:

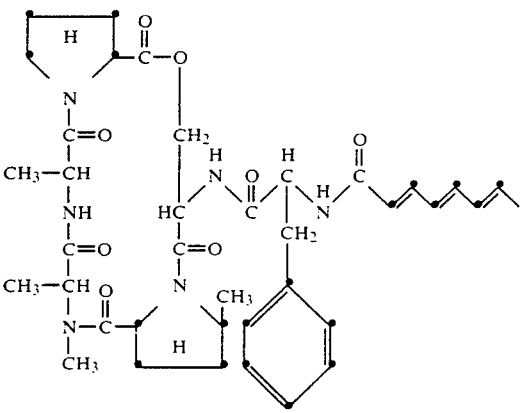

A54556 FACTOR B

Antibiotic A54556 factor B is a slightly yellowish colored, crystalline solid. Elemental analysis of A54556 factor B indicates that it has the following approximate percentage composition: 62.89 percent carbon, 6.89 percent hydrogen, 11.93 percent nitrogen, and 18.39 percent oxygen. As determined by electron impact and field desorption mass spectrometry, A54556 factor B has a molecular weight of 704. Based on the elemental analysis and the molecular weight, an empirical formula of $C_{37}H_{48}N_6O_8$ is assigned to factor B. Electrometric titration of factor B in 66 percent dimethylformamide in water showed no titratable groups.

Figure 2:
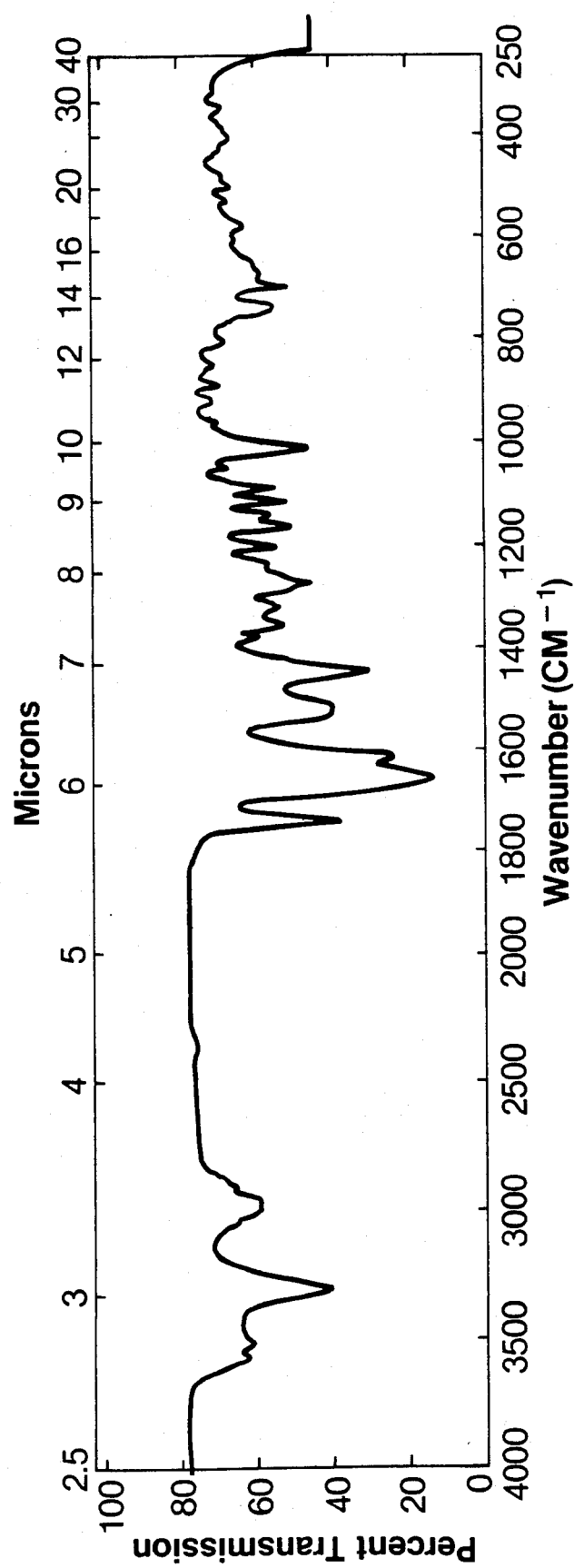

The infrared absorption spectrum of A54556 factor B is shown in the accompanying drawings as FIG. 2. The following distinguishable absorption maxima are observed: 3545 (very weak), 3480 (very weak), 3280 (medium), 2950 (weak), 1728 (medium), 1640 (strong), 1599 (medium strong), 1499 (medium), 1431 (medium), 1368 (weak), 1348 (weak), 1310 (very weak), 1273 (shoulder, very weak), 1265 (weak), 1225 (very weak), 1190 (weak), 1155 (weak), 1130 (very weak), 1106 (weak), 1078 (weak), 1038 (very weak), 1000 (medium weak), 950 (very weak), 910 (very weak), 880 (very weak), 840 (very weak), 798 (very weak), and 730 (weak) $cm^{-1}$.

The X-ray powder diffraction characteristics of antibiotic A54556 factor B (copper radiation, 1.5418λ, nickel filter, d=interplanar spacing in angstroms) are recorded in Table 9, which follows:

TABLE 9

| X-Ray Diffraction Characteristics for Antibiotic A54556 factor B | |
|---|---|
| Spacing d(A) | Intensities |
| 12.86 | very weak |
| 10.95 | strong |
| 9.91 | strong |
| 6.60 | weak |
| 6.31 | weak |
| 5.64 | medium |
| 5.15 | very weak |
| 4.74 | medium |
| 4.49 | very weak |
| 4.25 | medium b* |
| 3.92 | weak |
| 3.81 | weak |
| 3.57 | weak |
| 3.46 | very weak |
| 3.34 | weak |
| 3.13 | very weak |
| 3.05 | weak |
| 2.86 | very weak |
| 2.69 | very weak |
| 2.36 | very weak |
| 2.21 | very weak |

*b = broad
The intensities are estimated values.

The ultraviolet absorption maximum of A54556 factor B in ethanol is recorded in Table 6, above.

The amino-acid analysis of acid-hydrolyzed antibiotic A54556 factor B is set forth in Table 7, above.

The acyl moiety of factor B is identical to the acyl moiety of factor A, and has the same chemical shifts in the proton nuclear magnetic resonance spectrum, as determined in $CDCl_3$, and set forth above in the description of antibiotic A54556 factor A.

The chemical shifts of the amino acids of the peptide nucleus of antibiotic A54556 factor B, appearing in the proton nmr of factor B, determined at 298° K. in $CDCl_3$, are set forth in Table 10, which follows:

TABLE 10

| Chemical shifts of amino acids of Factors B and E | | | |
|---|---|---|---|
| Phenylalanine | | N—Methylalanine | |
| NH | 7.02 | N—CH3 | 2.84 |
| α | 4.67 | α | 4.78 |
| β's | 2.97 | β | 1.51 |
| Ring o- | 7.16 | | |
| m- | 7.29 | | |

TABLE 10-continued

| Chemical shifts of amino acids of Factors B and E | | | |
|---|---|---|---|
| p- | 7.20 | | |
| Serine | | Alanine | |
| NH | 6.85 | NH | 8.39 |
| α | 4.51 | α | 4.89 |
| β's | 4.83 | β | 1.37 |
|  | 3.60 | | |
| Proline | | Proline | |
| α | 4.45 | α | 5.15 |
| β's | 2.16 | β's | 2.36 |
|  | 1.98 |  | 1.98 |
| γ's | 1.98 | γ's | 2.16 |
|  | 1.88 |  | 1.98 |
| δ's | 3.60 | δ's | 3.74 |
|  | 3.30 |  | 3.60 |

Antibiotic A54556 factor B is soluble in the same solvents as is factor A.

Based on the physical chemical properties described above, the following structure is assigned to antibiotic A54556 factor B:

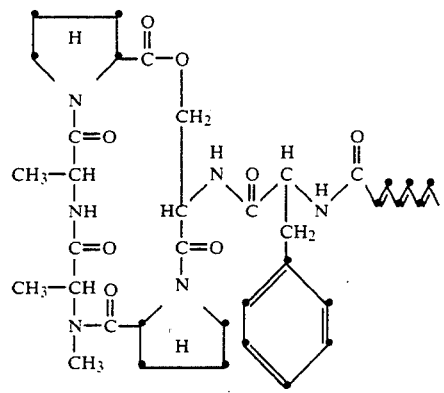

A54556 FACTOR C

Antibiotic A54556 factor C is a tan, amorphous solid. Elemental analysis of A54556 factor C indicates that it has the following approximate percentage composition: 62.65 percent carbon, 7.19 percent hydrogen, 12.14 percent nitrogen, and by difference, 18.02 percent oxygen. As determined by electron impact and field desorption mass spectrometry, A54556 factor C has a molecular weight of 692. Based on the elemental analysis and the molecular weight, an empirical formula of $C_{36}H_{48}N_6O_8$ is assigned to factor C. Electrometric titration of factor C in 66 percent dimethylformamide in water showed no titratable groups.

Figure 3:
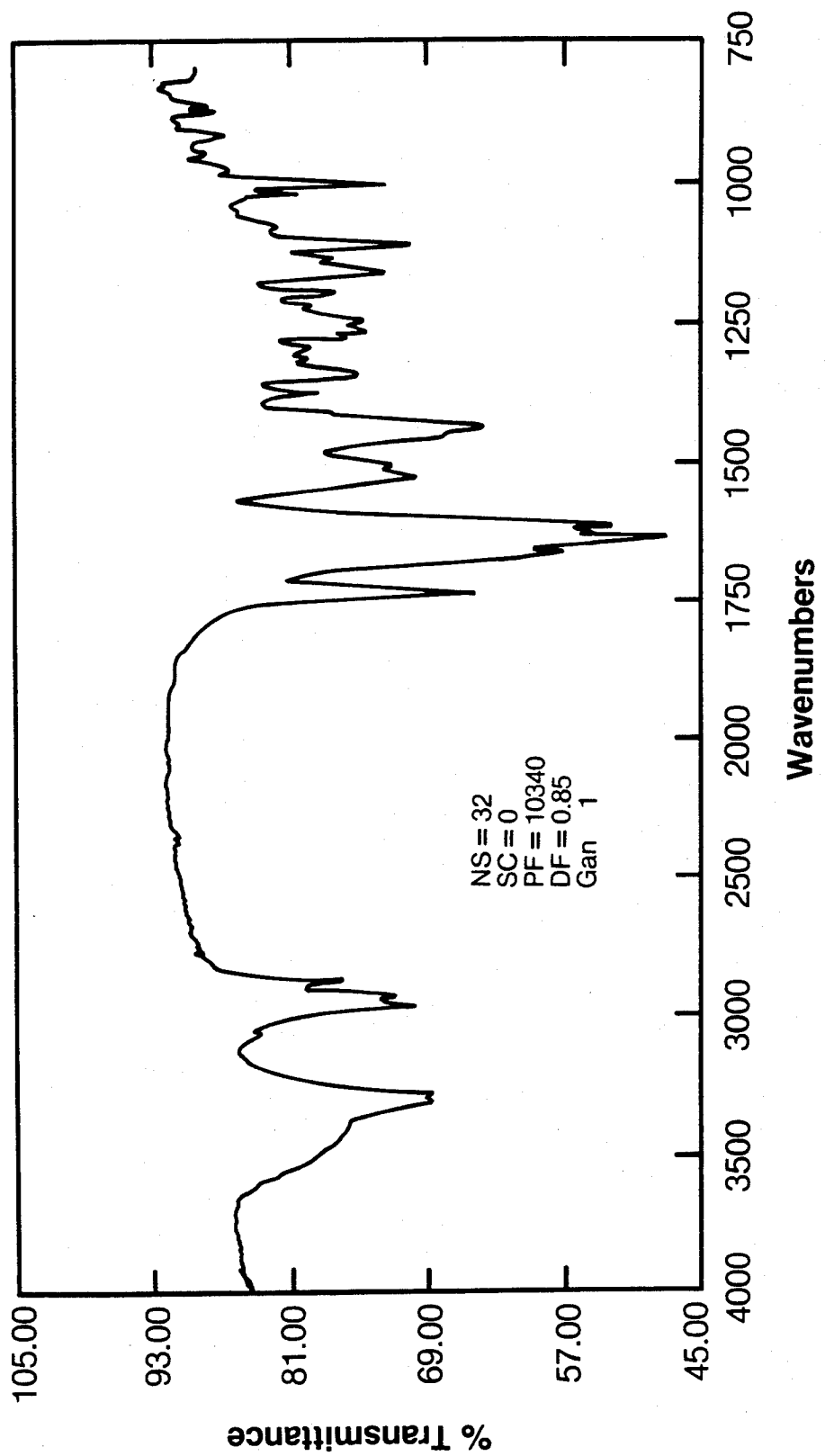

The infrared absorption spectrum of A54556 factor C is shown in the accompanying drawings as FIG. 3. The following distinguishable absorption maxima are observed: 3600–3200 (broad), 3318 (medium), 3282 (medium), 3061 (very weak), 2963 (medium), 2937 (medium), 2877 (weak), 1737 (medium strong), 1671 (strong), 1651 (very strong), 1638 (strong), 1624 (very strong), 1524 (medium), 1502 (medium weak), 1434 (medium), 1372 (medium weak), 1336 (medium weak), 1310 (weak), 1292 (weak), 1272 (medium), 1263 (medium), 1235 (medium), 1219 (weak), 1194 (medium weak), 1158 (medium), 1133 (weak), 1110 (medium), 1075 (weak), 1015 (weak), 999 (medium), 974 (weak), 948 (weak), 913 (weak), 871 (weak), and 856 (weak) $cm^{-1}$.

The ultraviolet absorption maximum of A54556 factor C in ethanol is recorded in Table 6, above.

The amino-acid analysis of acid-hydrolyzed antibiotic A54556 factor C is set forth in Table 7, above.

The acyl moiety of antibiotic A54556 factor C was identified by electron impact mass spectrometry and the ultraviolet absorption spectrum as having the following structure:

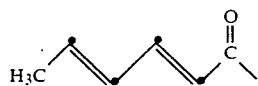

The chemical shifts of the amino acids of the peptide nucleus of antibiotic A54556 factor C are recorded in Table 8, above.

Antibiotic A54556 factor C is soluble in the same solvents as is factor A.

Based on the physical chemical properties described above, the following structure is assigned to antibiotic A54556 factor C:

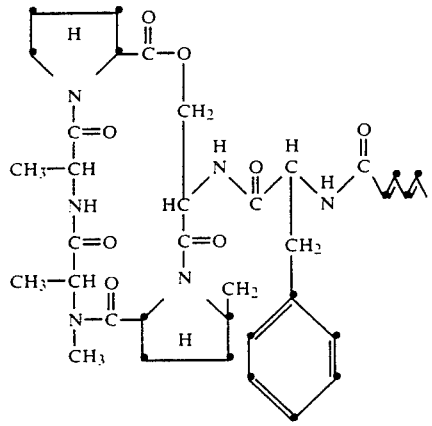

A54556 FACTOR D

Antibiotic A54556 factor D is a tan, amorphous solid. Elemental analysis of A54556 factor D indicates that it has the following approximate percentage composition: 61.24 percent carbon, 7.27 percent hydrogen, 10.60 percent nitrogen, and by difference, 20.89 percent oxygen. As determined by electron impact and field desorption mass spectrometry, A54556 factor D has a molecular weight of 720. Based on the elemental analysis and the molecular weight, an empirical formula of $C_{38}H_{52}N_6O_8$ is assigned to factor D. Electrometric titration of factor D in 66 percent dimethylformamide in water showed no titratable groups.

Figure 4:
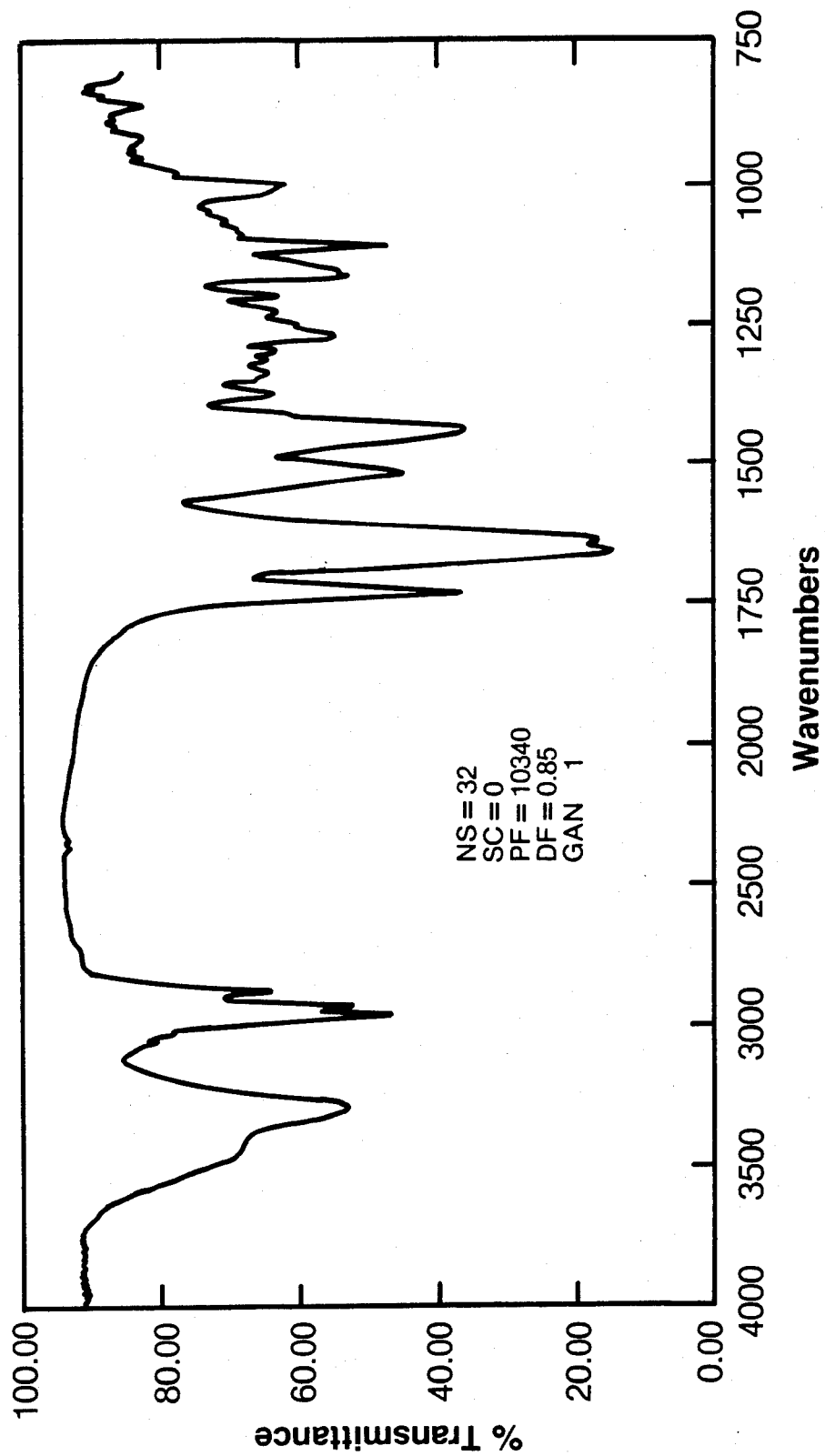

The infrared absorption spectrum of A54556 factor D is shown in the accompanying drawings as FIG. 4. The following distinguishable absorption maxima are observed: 3300 (medium), 2963 (weak), 2937 (weak), 2879 (medium), 1732 (medium strong), 1656 (strong), 1636 (strong), 1514 (medium strong), 1437 (medium strong), 1373 (medium weak), 1347 (very weak), 1333 (weak), 1295 (weak), 1270 (medium), 1246 (very weak), 1223 (weak), 1195 (medium), 1161 (medium), 1148 (medium), 1111 (medium), 1000 (medium), 976 (very weak), 948 (very weak), 912 (very weak), and 856 (very weak) $cm^{-1}$.

The ultraviolet absorption maximum of A54556 factor D in ethanol is recorded in Table 6, above.

The amino-acid analysis of acid-hydrolyzed antibiotic A54556 factor D is set forth in Table 7, above.

The acyl moiety of antibiotic A54556 factor D was identified by proton nmr, and has the following structure with the noted chemical shifts:

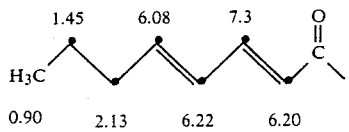

The chemical shifts of the amino acids of the peptide nucleus of antibiotic A54556 factor D are recorded in Table 8, above.

Antibiotic A54556 factor D is soluble in the same solvents as is factor A.

Based on the physical chemical properties described above, the following structure is assigned to antibiotic A54556 factor D:

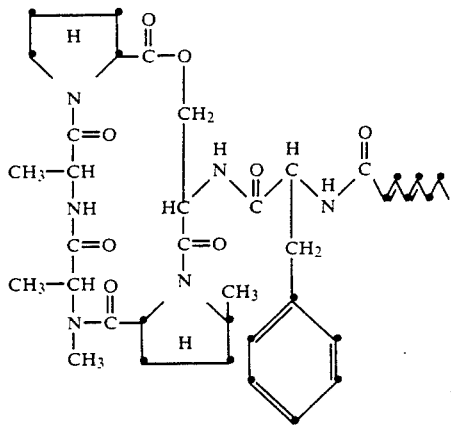

A54556 FACTOR E

Antibiotic A54556 factor E is a tan, amorphous solid. Elemental analysis of A54556 factor E indicates that it has the following approximate percentage composition: 61.74 percent carbon, 6.85 percent hydrogen, 10.54 percent nitrogen, and by difference, 20.87 percent oxygen. As determined by electron impact and field desorption mass spectrometry, A54556 factor E has a molecular weight of 678. Based on the elemental analysis and the molecular weight, an empirical formula of $C_{35}H_{46}N_6O_8$ is assigned to factor E. Electrometric titration of factor E in 66 percent dimethylformamide in water showed no titratable groups.

Figure 5:
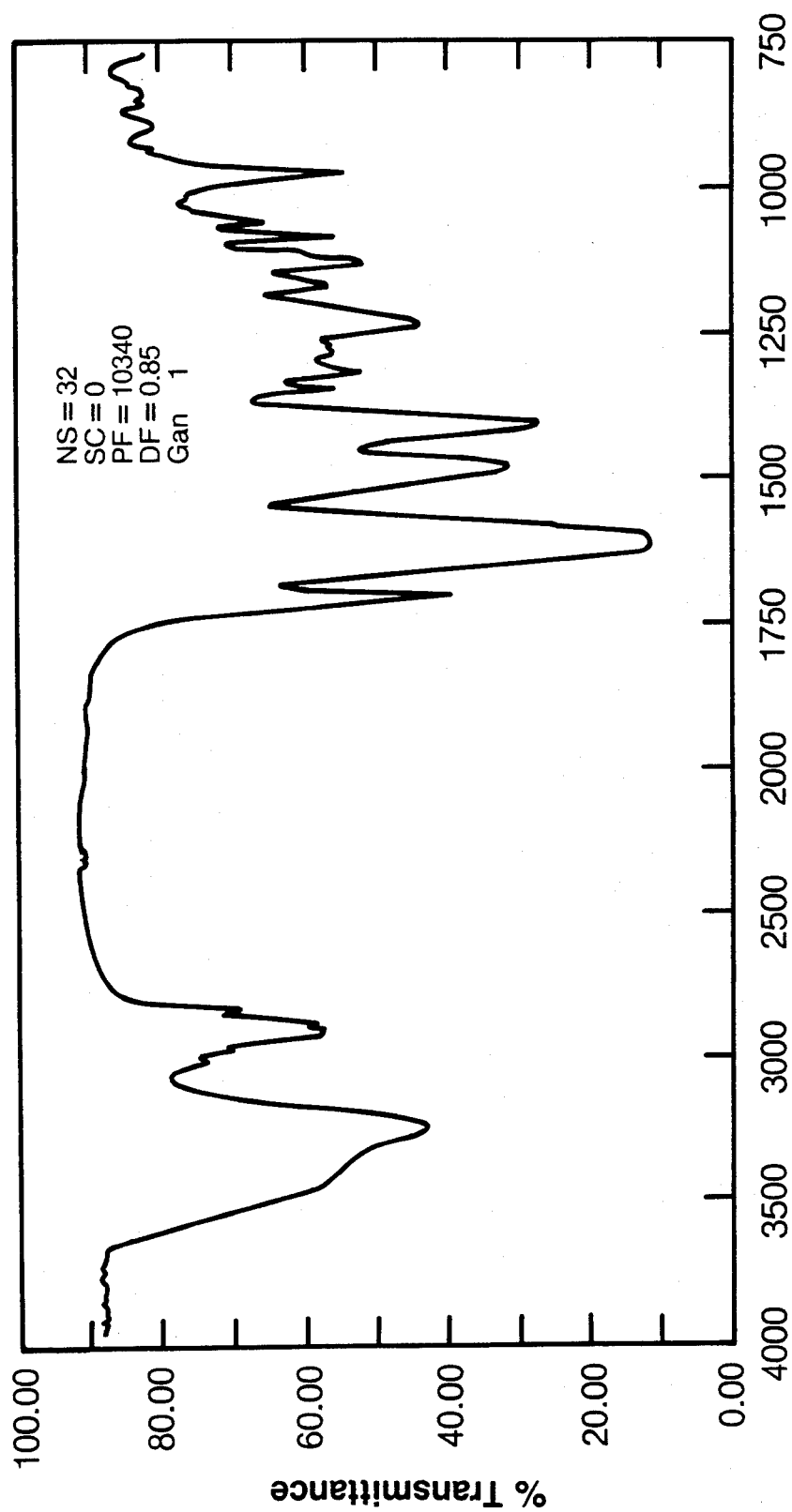

The infrared absorption spectrum of A54556 factor E is shown in the accompanying drawings as FIG. 5. The following distinguishable absorption maxima are observed: 3310 (medium), 3063 (very weak), 3027 (very weak), 2963 (medium), 2933 (medium), 2877 (weak), 1733 (medium strong), 1657 (very strong), 1635 (strong), 1514 (medium), 1441 (medium), 1373 (weak), 1347 (weak), 1313 (very weak), 1299 (very weak), 1195 (medium weak), 1159 (weak), 1110 (weak), 1084 (weak), 1003 (medium), 957 (very weak), and 916 (weak) $cm^{-1}$.

The ultraviolet absorption maximum of A54556 factor E in ethanol is recorded in Table 6, above.

The amino-acid analysis of acid-hydrolyzed antibiotic A54556 factor E is set forth in Table 7, above.

The acyl moiety of antibiotic A54556 factor E was identified by electron impact mass spectrometry and ultraviolet absorption spectrum as having the same structure as that of factor C.

The chemical shifts of the amino acids of the peptide nucleus of factor E are recorded in Table 10, above.

Antibiotic A54556 factor E is soluble in the same solvents as is factor A.

Based on the physical chemical properties described above, the following structure is assigned to antibiotic A54556 factor E:

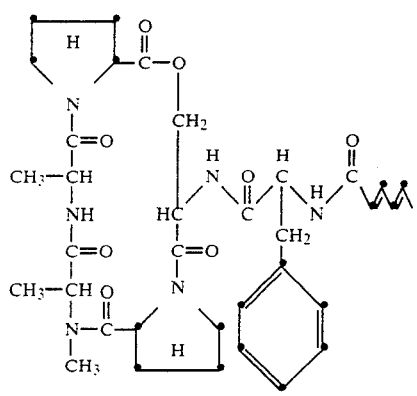

A54556 FACTOR H

Antibiotic A54556 factor H is a light tan, amorphous solid. Elemental analysis of A54556 factor H indicates that it has the following approximate percentage composition: 60.76 percent carbon, 6.57 percent hydrogen, 10.22 percent nitrogen, and, by difference, 22.45 percent oxygen. As determined by electron impact and field desorption mass spectrometry, A54556 factor H has a molecular weight of 708. Based on the elemental analysis and the molecular weight, an empirical formula of $C_{36}H_{48}N_6O_9$ is assigned to factor H. Electrometric titration of factor H in 66 percent dimethylformamide in water showed no titratable groups.

Figure 6:
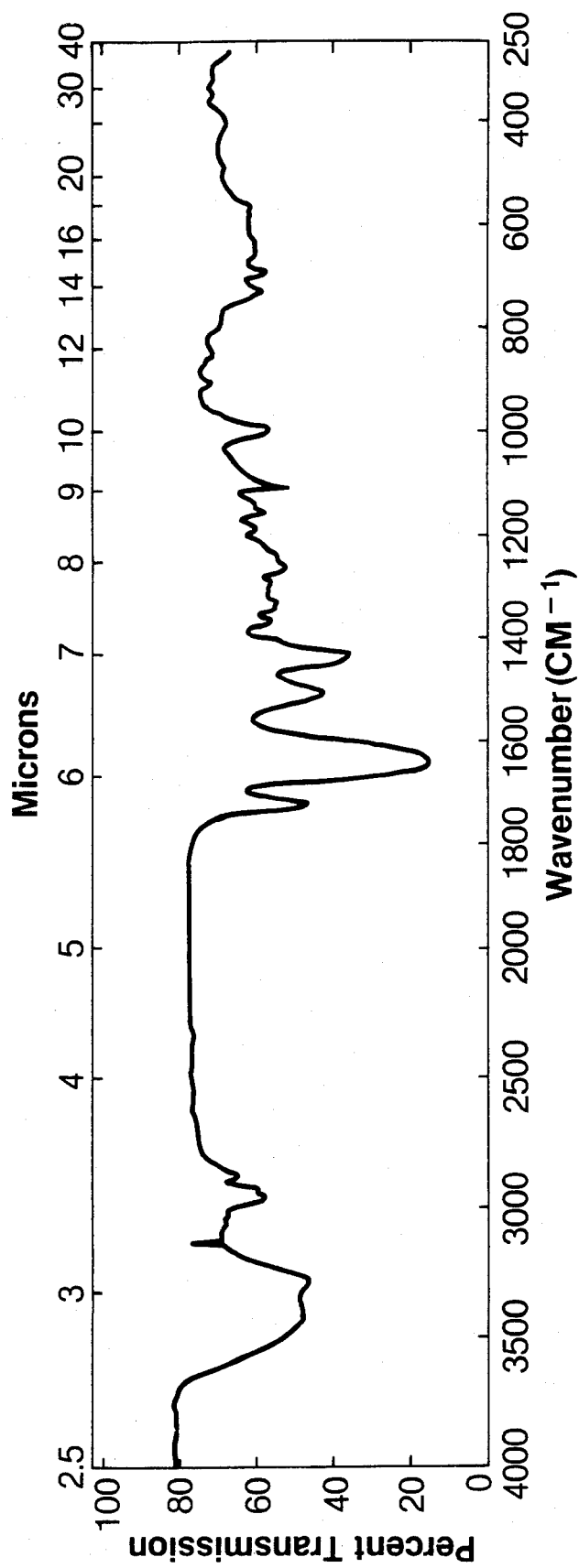

The infrared absorption spectrum of A54556 factor H is shown in the accompanying drawings as FIG. 6. The following distinguishable absorption maxima are observed: 3410 (broad band), 3285 (medium), 2964 (weak), 2880 (weak), 1725 (medium), 1645 (strong), 1560 (weak), 1435 (medium weak), 1373 (weak), 1340 (broad, weak), 1292 (very weak), 1265 (weak), 1240 (shoulder, weak), 1190 (very weak), 1155 (very weak), 1105 (weak), 998 (weak), 969 (shoulder), 907 (very weak), and 850 (very weak) $cm^{-1}$.

The ultraviolet absorption maximum of A54556 factor H in ethanol is recorded in Table 6, above.

The amino-acid analysis of acid-hydrolyzed antibiotic A54556 factor H is set forth in Table 7, above.

The acyl moiety of antibiotic A54556 factor H was identified by proton nmr, and has the following structure with the noted chemical shifts:

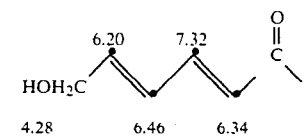

The chemical shifts of the amino acids of the peptide nucleus of antibiotic A54556 factor H are recorded in Table 8, above.

Antibiotic A54556 factor H is soluble in the same solvents as is factor A.

Based on the physical chemical properties described above, the following structure is assigned to antibiotic A54556 factor H:

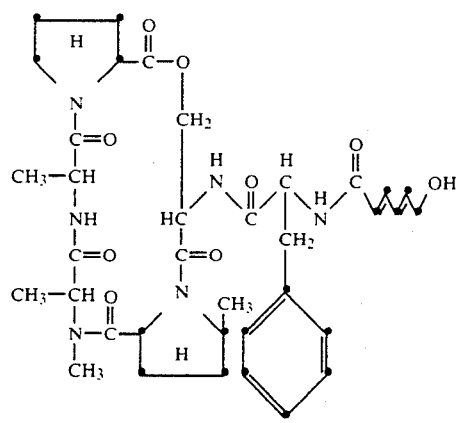

Two additional factors, denominated A54556 factor F, and A54556 factor G, respectively, have thus far been characterized chromatographically only.

The A54556 factors may be separated by high performance liquid chromatography (HPLC), using reversed phase silica gel (Ultrasphere ODS, from Altex Scientific, Inc., a subsidiary of Beckman Instruments, Inc.). In Table 11, which follows, are given the retention times for some of the A54556 factors in a representative separation by HPLC, using the following conditions:

Column Size: 4.6×250 mm. (Stainless steel)
Packing: Silica gel (Ultrasphere ODS, 5 microns)
Solvent: Methanol:water (75:25); Flow Rate: 1.0 ml./min.; Chart speed: 120 secs./cm.
Detector: LDC-UV Monitor at 280 nm.

TABLE 11

| A54556 Factor | Retention Time (minutes) | Relative Retention |
|---|---|---|
| A | 20.4 | 4.6 |
| B | 16.1 | 3.7 |
| C | 11.4 | 2.6 |
| D | 27.0 | 6.1 |
| E | 9.3 | 2.1 |
| H | 4.4 | 1 |

The A54556 factors can also be separated by high-performance-low-pressure-liquid-chromatography (HPLPLC), described hereinafter in Example 3.

Antibiotic A54556 complex and factors are active against gram-positive microorganisms, including Staphylococcus and Streptococcus species, and are active against penicillin and methicillin resistant organisms.

The activity of A54556 complex and the individual factors has been demonstrated by a number of tests which are described hereinafter.

DISC-PLATE SENSITIVITY PROCEDURE

Agar plates, inoculated with the test organism, were used; 6 mm. discs (0.2 ml. capacity) were saturated from log 2 dilutions of the antibiotic solution. Disc contents of 1/5 and 1/50 of the concentration of the solution of the antibiotic were used. Thus, disc contents of 300 and 30 mcg., respectively, were obtained from a solution of 1500 mcg./ml. concentration of the antibiotic. Activity is reported as the diameter, measured in millimeters (mm.), of the zone of inhibition produced by the different concentrations of the antibiotic in mcg./disc, as recorded in Table 12, which follows:

TABLE 12
ACTIVITIES OF A54556 COMPLEX AND FACTOR A

| Test Organism | Rate (mcg./disc) | Zone diameter (mm.) at mcg./disc | |
|---|---|---|---|
| | | Complex | Factor A |
| Staphylococcus aureus 3055* | 30 | 12.1 | 19.2 |
| | 300 | 18.9 | 24.3 |
| Staphylococcus aureus 3074** | 30 | 14.8 | 18.3 |
| | 300 | 19.2 | 20.9 |
| Staphylococcus aureus 3130*** | 30 | 17.1 | 21.7 |
| | 300 | 22.2 | 25.5 |
| Streptococcus pyogenes (Group A) C203 | 30 | 18.0 | 24.0 |
| | 300 | 23.0 | 30.0 |
| Streptococcus sp. (Group D) 9960 300 | 30 | 18.3 | 22.4 |
| | 23.3 | 28.0 | |
| Streptococcus pneumoniae Park I | 30 | 20.0 | 26.0 |
| | 300 | 24.0 | 34.0 |

*benzylpenicillin-susceptible
**benzylpenicillin-resistant
***benzylpenicillin-resistant, methicillin-resistant A second disc-plate test was run, this time on the complex and all factors which had been isolated, following the same procedure as described hereinbefore. The results are set forth in Table 13, which follows:

TABLE 13
ACTIVITIES OF A54556 COMPLEX AND FACTORS

| Test Organism | Rate mcg./disc | A | B | C | D | E | F | H | Complex |
|---|---|---|---|---|---|---|---|---|---|
| Staphylococcus aureus 3055* | 30 | 19 | 18 | 21 | 29 | 17 | 15 | 8 | 22 |
| | 300 | 24 | 26 | 25 | 30 | 23 | 23 | 11 | 28 |
| | 30 | 21 | 20 | 23 | — | 15 | — | — | — |
| | 300 | 28 | 26 | 31 | — | 23 | — | — | — |
| Staphylococcus aureus V41** | 30 | 20 | 15 | 21 | 27 | 17 | 13 | 10 | 22 |
| | 300 | 27 | 19 | 30 | 28 | 27 | 20 | 14 | 29 |
| | 30 | 22 | 18 | 24 | — | 13 | — | — | — |
| | 300 | 33 | 26 | 25 | — | 23 | — | — | — |
| Staphylococcus epidermidis 300 EPI1 | 30 | 20 | 13 | 21 | 25 | 13 | 12 | 12 | 21 |
| | 22 | 21 | 26 | 34 | 25 | 24 | 24 | 25 | |
| | 30 | 20 | 16 | 23 | — | 11 | — | — | — |
| | 300 | 28 | 27 | 24 | — | 24 | — | — | — |
| Streptococcus sp. (Group D) X66 | 30 | 23 | 22 | 24 | 26 | 22 | 22 | 21 | 29 |
| | 300 | 33 | 27 | 25 | 33 | 28 | 36 | 27 | 33 |
| | 30 | 28 | 23 | 25 | — | 21 | — | — | — |
| | 300 | 29 | 30 | 35 | — | 27 | — | — | — |
| Streptococcus pneumoniae Park I | 30 | 18 | 20 | 25 | 30 | 25 | 23 | 25 | 30 |
| | 300 | 33 | 32 | 30 | 34 | 35 | 30 | 36 | 35 |
| | 30 | 22 | 25 | 30 | — | 22 | — | — | — |
| | 300 | 35 | 35 | 35 | — | 28 | — | — | — |
| Streptococcus pyogenes C203 | 30 | 20 | 18 | 22 | 24 | 20 | 20 | 30 | 26 |
| | 300 | 30 | 24 | 30 | 32 | 30 | 30 | 32 | 35 |
| | 30 | 25 | 26 | 28 | — | 18 | — | — | — |
| | 300 | 32 | 30 | 33 | — | 24 | — | — | — |

*benzylpenicillin-susceptible
**benzylpenicillin-resistant
— not tested

Antibiotic A54556 factors A, B, C, D, E, F, G, and H have been tested and found to be active against a number of anaerobic bacteria, as recorded in Table 14, which follows, the MIC values having been determined by the agar-dilution method.

TABLE 14
ACTIVITY OF A54556 FACTORS AGAINST ANAEROBIC BACTERIA

| Test Organism | MIC (μg./ml.) | | | | | | | |
|---|---|---|---|---|---|---|---|---|
| | A | B | C | D | E | F | G | H |
| Clostridium difficile 2994 | >128 | >128 | >128 | >128 | >128 | >128 | >128 | >128 |
| Clostridium perfringens 81 | >128 | 16 | >128 | >128 | >128 | 32 | >128 | >128 |
| Clostridium septicum 1128 | >128 | 16 | >128 | >128 | >128 | 32 | >128 | >128 |
| Eubacterium aerofaciens 1235 | >128 | 16 | >128 | >128 | >128 | 32 | >128 | >128 |
| Peptococcus asaccharolyticus 1302 | >128 | 8 | 16 | 128 | 64 | 16 | 128 | >128 |
| Peptococcus prevoti 1281 | >128 | 8 | >128 | >128 | 128 | 16 | 128 | >128 |
| Peptostreptococcus anaerobius 1428 | >128 | 8 | >128 | 128 | >128 | 128 | 16 | 128 |
| Peptostreptococcus intermedius 1264 | >128 | >128 | >128 | >128 | >128 | >128 | >128 | >128 |
| Propionibacterium acnes 79 | >128 | >128 | 32 | >128 | >128 | >128 | >128 | >128 |
| Bacteroides fragilis 111 | >128 | 32 | >128 | >128 | >128 | 128 | 32 | >128 |
| Bacteroides fragilis 1877 | >128 | >128 | >128 | >128 | >128 | >128 | >128 | >128 |
| Bacteroides fragilis 1936B | >128 | 16 | >128 | >128 | >128 | >128 | >128 | >128 |
| Bacteroides thetaiotaomicron 1438 | >128 | 16 | >128 | >128 | >128 | >128 | >128 | >128 |
| Bacteroides melaninogenicus 1856/28 | >128 | >128 | >128 | >128 | >128 | >128 | >128 | >128 |
| Bacteroides melaninogenicus 2736 | >128 | >128 | >128 | >128 | >128 | >128 | >128 | >128 |
| Bacteroides vulgatis 1211 | >128 | 32 | >128 | >128 | >128 | >128 | >128 | >128 |
| Bacteroides corrodens 1874 | >128 | >128 | >128 | >128 | >128 | >128 | >64 | >128 |
| Fusobacterium symbiosum 1470 | >128 | 8 | >128 | >128 | 128 | 16 | >128 | >128 |
| Fusobacterium necrophorum 6054A | >128 | 16 | >128 | >128 | >128 | 16 | >128 | >128 |

The antibiotic A54556 complex and factors A, B, C, D, E, and H have shown in vivo antimicrobial activity against experimental bacterial infections. When two doses of test compound were administered subcutaneously to mice in illustrative infections, the activity is measured as an $ED_{50}$ value [effective does in mg./kg. to protect fifty percent of the test animals: See Warren Wick et al., *J. Bacteriol.* 81, 233–235 (1961)]. The $ED_{50}$ values for these antibiotic A54556 factors are recorded in Table 15, which follows.

TABLE 15

$ED_{50}$ Values For A54556 Factors

| Antibiotic A54556 Factor | Staph. sureus $ED_{50}$ | S. pyogenes $ED_{50}$ | S. pneumoniae $ED_{50}$ |
| --- | --- | --- | --- |
| Complex | 17.5 | 52.5 | >70 |
| A | | >70 | |
| B | | >70 | |
| C | | 11.1 | |
| D | | >70 | |
| E | | >70 | |
| H | | 9.9 | |

The $LD_{50}$, intraperitoneally in mice, of the complex has been determined to be >300 mg./kg.×1.

While the A54556 antibiotic complex and the individual factors show activity against gram-positive organisms, the A54556 complex and the individual factors are inactive against fungi, and show only a low order of activity against gram-negative organisms.

The A54556 antibiotics are useful for suppressing the growth of Staphylococcus and Streptococcus organisms. These organisms grow on the surface of the skin, and the antibiotics could therefore be used, for example, in the treatment of acne. The A54556 antibiotic complex, in purified form, or the individual factors, in purified form, can be formulated in pharmaceutically-acceptable diluents such as isopropyl alcohol for application to the skin. Such solutions can be made up with antibiotic concentrations of from about 1 to about 15 percent weight per volume. Alternatively, these antibiotics can be made up into creams or lotions for application to the skin.

The Culture A54556, classified as a strain of *Streptomyces hawaiiensis* Cron, Whitehead, Hooper, Heinemann and Lein 1956, ATCC 12236, has been deposited and made a part of the stock culture collection of the Northern Regional Research Center, U.S. Department of Agriculture, Agricultural Research Service, Peoria, Ill., 61604, from which it is available under the number NRRL 15010.

As is the case with other organisms, the characteristics of *S. hawaiiensis* NRRL 15010 are subject to variation. For example, mutants (spontaneous or induced), transconjugants and recombinants (including recombinant DNA on plasmids) of the NRRL 15010 strain, or derived from this strain, may be used in this invention.

The A54556 complex is produced by culturing the previously undescribed microorganism *Streptomyces hawaiiensis* NRRL 15010, or an A54556-producing mutant or variant thereof, in a culture medium containing assimilable sources of carbon, nitrogen, and inorganic salts, under submerged aerobic fermentation conditions until a substantial level of antibiotic activity is produced.

A number of different media may be used to grow *S. hawaiiensis* NRRL 15010. These media should contain assimilable sources of carbon, nitrogen, and inorganic salts. Suitable carbon sources include glucose, starch, and dextrin. Suitable nitrogen sources include peptone, enzyme-hydrolyzed casein, beef extract, and soybean grits.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of the A54556 antibiotics, submerged aerobic fermentation in stirred vessels is utilized. However, small amounts of the A54556 antibiotics may be obtained by shake-flask culture. For large volume fermentations, it is preferable to use a vegetative inoculum. The vegetative inoculum is prepared by inoculating a small volume of culture medium with the spore form, mycelial fragments, or a lyophilized pellet of the organism to obtain a fresh, actively growing culture. The vegetative inoculum is then transferred to a fermentation vessel where, after a suitable incubation time, the A54556 complex is produced in optimal yield.

The pH of the uninoculated fermentation medium varies with the medium used for production, but the pH of all of the fermentation media falls in the range of from about pH 6.5 to about pH 7.0.

Optimum production of A54556 antibiotic complex appears to occur at a temperature of about 30° C.

As is customary in aerobic submerged culture processes, sterile air is dispersed through the culture medium. For efficient growth of the organism, the volume of the air used is in the range of from about 0.25 to about 0.5 volume of air per volume of culture medium per minute (v/v/m). An optimum rate in a 100-liter vessel is about 0.25 v/v/m with agitation provided by conventional impellers rotating at about 200 RPM. It may be necessary to add small amounts (i.e., 0.2 ml/L.) of an antifoam agent such as polypropylene glycol to large-scale fermentation media if foaming becomes a problem.

Production of the A54556 antibiotics can be monitored during the fermentation by either agar diffusion or turbidimetric methods. Test organisms suitable for use include *Staphylococcus aureus* (XI), *Bacillus subtilis*, *Bacillus megaterium*, and *Micrococcus luteus*.

Antibiotic activity is generally present after about 24 hours and remains present for at least 4 or more days during the fermentation period. Peak antibiotic production occurs in from about 2 to about 4 days fermentation time.

The A54556 antibiotics can be recovered from the fermentation medium by methods known in the art.

The antibiotic activity is present in the liquid portion of the broth, so the mycelia are removed by filtering on a filter press using 5 percent filter aid (Hyflo Supercel, Johns-Manville Corp.), and the mycelia discarded. The antibiotic activity is then recovered from the filtrate by extraction with a water-immiscible organic solvent such as ethyl acetate. The ethyl acetate extract is concentrated in vacuo to an oily residue which is dissolved in chloroform. The antibiotic complex is then isolated from the chloroform solution by column chromatography using chloroform and mixtures of chloroform:methanol, successively, as the eluting agent.

Suitable adsorbents include silica gel, carbon, alumina, anion and cation exchange resins, polyamide, carboxymethylcellulose, highly porous copolymers of styrene and divinylbenzene such as Diaion HP-20, the Amberlite XAD resins, and the Duolite resins such as ES-865 and the like, as well as Sephadex resins, the hydrophilic, insoluble, molecular-sieve chromatographic mediums made by cross-linking dextran, and also TSK Gels. The Diaion resins are a product of Mitsubishi Chemical Industries, Limited, Tokyo, Japan. The Amberlite XAD resins are produced by Rohm and Haas, Philadelphia, Pa. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, and from Bio-Rad, 2200 Wright Ave., Richmond, Calif., 94804.

The A54556 antibiotic complex can be further purified and separated into its individual factors by chromatographic techniques.

In order to illustrate more fully the operation of this invention, the following Examples are provided.

EXAMPLE 1

A. Preparation of First Stage Inoculum

A medium was prepared for use in the agar slant culture of *Streptomyces hawaiiensis* NRRL 15010:

| Ingredient | Amount (g./L.) |
| --- | --- |
| Dextrin[1] | 10.0 |
| Yeast extract | 1.0 |
| Enzyme-hydrolyzed casein[2] | 2.0 |
| Beef extract | 1.0 |
| $CoCl_2.6H_2O$ | 0.01 |
| Washed agar | 20.0 |
| Deionized water | q.s. to 1 liter |

[1]Metheson Coleman and Bell, Norwood, Ohio.
[2]N—Z—Amine A (Sheffield Products Co., Memphis, Tenn.)

The pH of the medium was adjusted to 7.0 with aqueous sodium hydroxide before autoclaving; after autoclaving, the pH was 6.8.

Spores of Culture NRRL 15010 were inoculated on a nutrient agar slant made up of the above-identified ingredients, and the thus-inoculated slant was incubated for from about 7 to about 10 days at a temperature of about 30° C. The mature slant culture was covered with water and scraped with a sterile tool to loosen the spores and the mycelium. The spores and mycelia were then suspended in calf serum and lyophilized to form a pellet. The pellet was used to inoculate 50 ml. of a medium having the following composition:

| Ingredient | Amount (g./L.) |
| --- | --- |
| Glucose | 15.0 |
| Tapioca dextrin | 20.0 |
| Soybean grits | 15.0 |
| Corn steep liquor | 10.0 |
| Yeast extract | 1.0 |
| $CaCO_3$ | 2.0 |
| Tap water | q.s. to 1 liter |

The pH of the medium was adjusted to 6.5 with aqueous sodium hydroxide before autoclaving; after autoclaving, the pH was 6.7.

The inoculated medium was incubated in a 250-ml. wide-mouth Erlenmeyer flask at 30° C. for about 50 hours on a shaker rotating through an arc 2 inches in diameter at 250 RPM.

This incubated medium is used either to inoculate small fermenters (the inoculum being approximately 1% per volume of medium) or to inoculate a second stage medium for the production of a larger volume of culture.

B. Preparation of Second Stage Inoculum

In order to provide a larger volume of inoculum, 2.5 ml. of incubated medium, prepared as described above, was used to inoculate 400 ml. of a second-stage growth medium having the same composition as that of the medium above. This second-stage medium was incubated in a wide-mouth 2-liter flask for about 24 hours at 30° C. on a shaker rotating through an arc 2 inches in diameter at 250 RPM.

C. Fermentation of NRRL 15010

Incubated second-stage medium (800 ml.) thus prepared was used to inoculate 100 liters of sterile production medium having the following composition:

| Ingredient | Amount (g./L.) |
| --- | --- |
| Silicone antifoam agent[1] | 0.2 |
| Glucose | 25.0 |
| Starch | 10.0 |
| Meat peptone[2] | 10.0 |
| Enzyme-hydrolyzed casein[3] | 4.0 |
| Blackstrap molasses | 5.0 |
| $MgSO_4.7H_2O$ | 0.5 |
| $CaCO_3$ | 2.0 |
| Czapek's mineral stock | 2.0 ml. |
| Tap water | q.s. to 100 liters |

[1]Dow-Corining Antifoam A
[2]O. M. Peptone (Amber Laboratories, Juneau, Wisc.)
[3]N—Z—Amine A (Sheffield Products Co., Memphis, Tenn.)

Before sterilization, the medium had pH 6.7. The medium, after being sterilized for 45 minutes at a temperature of about 121° C. and a pressure of 17–19 psi., had pH 6.5.

The inoculated and sterilized medium was allowed to ferment in a 165-liter fermentation tank for about 3–4 days at a temperature of 30° C. The fermentation medium was aerated with sterile air at the rate of 0.125 v/v/m and was stirred with conventional agitators at 150 RPM.

EXAMPLE 2

Isolation of A54556 Antibiotic Complex

Two hundred liters of whole fermentation broth was filtered using 5 percent filter aid (Hyflo Supercel, Johns-Manville Corp.) in a filter press to give 185 liters of filtrate. This filtrate was extracted successively at broth pH with an equal volume (Extract 1), and one-half volume (Extract 2) of ethyl acetate. The combined extracts, which contained the bulk of the antibiotic activity, were concentrated at reduced pressure to a volume of 600 ml.

This concentrate was then combined with an equivalent concentrate from the work-up of another 200-liter fermentation. The combined concentrates were filtered, concentrated to an oily residue, and the residue was dissolved in 600 ml. of methanol. The methanolic solution was added to 1500 ml. of diethyl ether, and the mixture filtered. The filtrate was concentrated at reduced pressure to an oily residue, which residue was dissolved in 1400 ml. of chloroform.

This chloroform solution was divided into two equal portions. Each portion was loaded onto a 14×32 cm. chromatography column containing dry silica gel (Grace 62), and each column was eluted sequentially with the following solvents: 8 liters of chloroform, 8 liters of chloroform:methanol (98:2), 8 liters of chloroform:methanol (95:5), and 4 liters of chloroform:methanol (90:10), with 500-ml. fractions being collected. The active fractions were determined by biological assay using *Staphylococcus aureus* X1 in agar trays. The inactive fractions were discarded.

The active fractions were combined and concentrated in vacuo to an oil. This oil was dissolved in 3 liters of diethyl ether and filtered. The filtrate was added to 4 liters of n-hexane, and a precipitate formed.

The precipitate was recovered by filtration and dried. There were obtained 21 g. of antibiotic A54556 complex. Concentration of the filtrate yielded an additional 8.5 g. of antibiotic A54556 complex, for a total yield of 29.5 g.

EXAMPLE 3

Isolation of A54556 Factors A, B, C, D, and E

A 2.0-g. portion of the 21.0 g. of A54556 complex of Example 2 was dissolved in 43 ml. of methanol:water (7:3). The solution was filtered and applied to a 4.7 (I.D.)×45.0 cm. Michel-Miller glass chromatography column (Ace Glass, Inc., Vineland, N.J.) packed with 10-20 micron LP−1/$C_{18}$ reversed-phase silica gel which was prepared in our laboratories by a special procedure described in Examples 6 and 7 of U.S. Pat. No. 4,299,763 (Nov. 10, 1981), which published description is hereby incorporated into and made a part of the present application. The column was eluted at 8.5 ml./min. with methanol:water (7:3), using an FMI pump. Fractions, 17-ml. each, were taken. The eluate was monitored at 280 nm using an ISCO Model UA-5 UV detector. The active fractions were located using S. aureus X1 agar plates as previously described.

Selected fractions were analyzed for the presence of the various factors using analytical high-performance-low-pressure-liquid-chromatography (HPLPLC). The selected fractions were applied to a 1×25 cm. glass chromatography column packed in our laboratories with 15-25 micron LiChroprep RP-18 [hydrocarbon phase ($C_{18}$) chemically bonded to silica gel, from MC/B Manufacturing Chemists, Inc., Cincinnati, Ohio]. An FMI valveless piston pump (Fluid Metering Inc., Oyster Bay, N.Y. 11771) was used to elute the column at 2.5 ml./min. (150 pis) with methanol:water (75:25). The eluate was monitored at 280 nm using an ISCO Model UA-5 UV detector. The results are summarized in Table 16, which follows:

TABLE 16

| Factor | Time in Seconds |
|--------|-----------------|
| A      | 1180            |
| B      | 960             |
| C      | 672             |
| D      | 1392            |
| E      | 632             |
| F      | 560             |
| G      | 474             |
| H      | 388             |

Fractions containing the individual factors were combined, concentrated at reduced pressure to a small volume, and lyophilized. The results are shown in Table 17, which follows:

TABLE 17

| Recovery of A54556 Factors | | |
|--------|-----------|---------|
| Factor | Fractions | Wt. (mg.) |
| A | 158-220 | 822 |
| B | 130-147 | 150 |
| C | 99-119 | 174 |
| D | 242-310 | 95 |
| E | 81-93 | 40 |

EXAMPLE 4

Isolation of A54556 Factor H

Crude A54556 antibiotic complex, 10.9 g., was dissolved in 250 ml. of methanol:water (7:3) and filtered. The filtrate was applied to a stainless steel column (8×100 cm.) packed with 4 liters of 10-20 micron LP-1/$C_{18}$ reversed-phase silica gel which was prepared in our laboratories as described in Example 3, above. The column was part of a Chromatospac Prep-100 unit (Jobin Yvon, 16–18 Rue du Canal, 91160 Longjumeau, France). The column was eluted at 60 ml./min. with methanol:water (7:3), collecting 200-ml. fractions at a flow rate of 50 ml./min. The eluate was monitored at 280 nm using an ISCO UV monitor.

The active fractions were located using S. aureus X1 on agar plates, as described above, and selected fractions were analyzed for the presence of the various fractions using analytical HPLPLC, as previously described. Fractions 19-21, inclusive, were combined, concentrated, and dissolved in a small volume of t-butyl alcohol. The solution was lyophilized to yield 633 mg. of crude antibiotic A54556 factor H.

This crude factor H was dissolved in 15 ml. of methanol:water (7:3), the solution filtered, and applied to a 3.7 cm. (I.D.)×35.0 cm. Michel-Miller glass chromatography column packed with reversed-phase silica gel as described in Example 3. The column was eluted at 5 ml./min. with methanol:water (7:3) using an FMI pump. One fraction was taken every 2 minutes. The fractions containing the antibiotic activity were detected employing S. aureus X1, as described above. Fractions 39-47, inclusive, were combined, dissolved in t-butyl alcohol, and lyophilized to yield 205 mg. of antibiotic A54556 factor H, as a tan, amorphous solid.

We claim:

1. A54556 Factor A, which has the structure

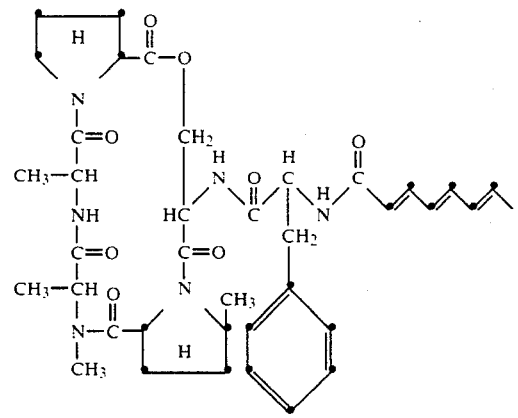

2. A54556 Factor B, which has the structure

3. A54556 Factor C, which has the structure
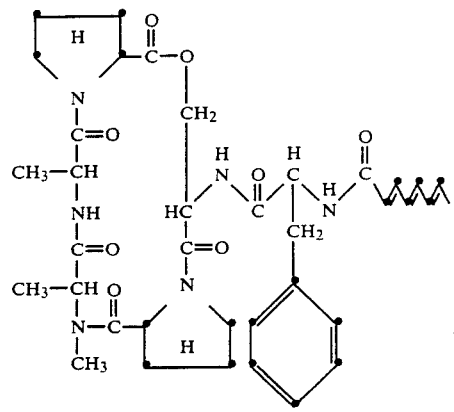
4. A54556 Factor D, which has the structure
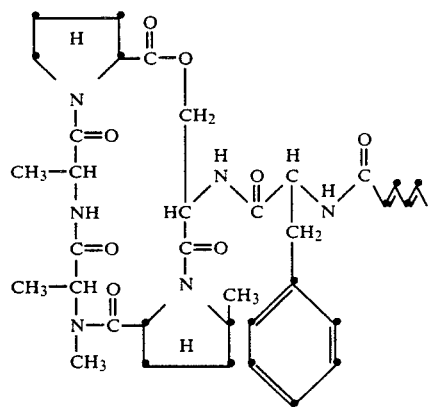
5. A54556 Factor E, which has the structure
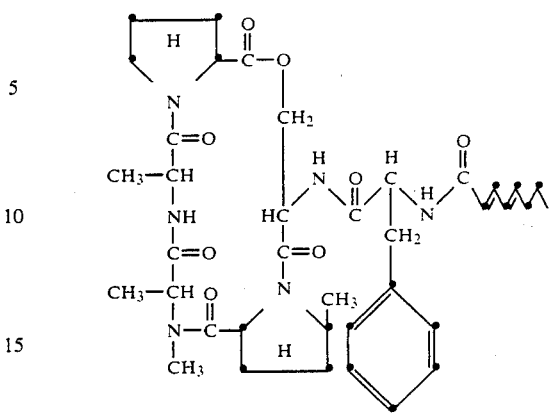
6. A54556 Factor H, which has the structure
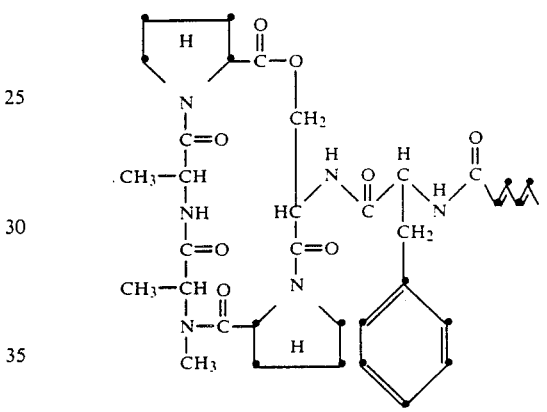
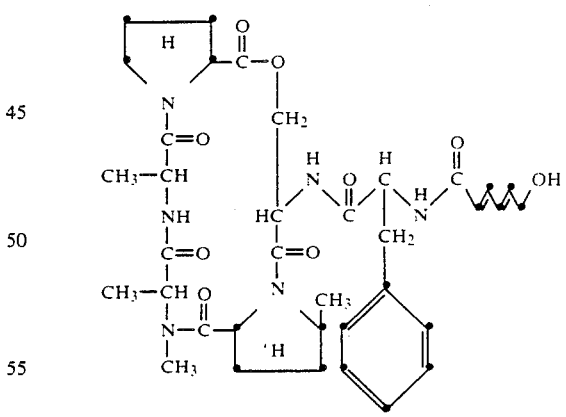
* * * * *